US009585908B1

(12) United States Patent
Beck et al.

(10) Patent No.: US 9,585,908 B1
(45) Date of Patent: Mar. 7, 2017

(54) COLLYRIUM COMPOSITION AND METHOD OF USING SAME

(71) Applicant: Chromaceutical Advanced Technologies, Inc., Hopkinton, MA (US)

(72) Inventors: Robert A. Beck, Framingham, MA (US); Robert A. Mateer, Jr., Douglas, MA (US)

(73) Assignee: Chromaceutical Advanced Technologies, Inc., Douglas, MA (US)

( * ) Notice: Subject to any disclaimer, the term of this patent is extended or adjusted under 35 U.S.C. 154(b) by 0 days.

(21) Appl. No.: 14/628,734

(22) Filed: Feb. 23, 2015

Related U.S. Application Data

(62) Division of application No. 13/291,687, filed on Nov. 8, 2011.

(60) Provisional application No. 61/411,073, filed on Nov. 8, 2010.

(51) Int. Cl.
*A61K 31/714* (2006.01)
*A61K 9/00* (2006.01)

(52) U.S. Cl.
CPC .......... *A61K 31/714* (2013.01); *A61K 9/0048* (2013.01)

(58) Field of Classification Search
None
See application file for complete search history.

(56) References Cited

U.S. PATENT DOCUMENTS

| 3,903,253 A | | 9/1975 | Rolland | |
|---|---|---|---|---|
| RE28,873 E | * | 6/1976 | Morgan | 604/298 |
| 5,801,161 A | | 9/1998 | Merkus | |
| 5,834,448 A | | 11/1998 | Pouchol et al. | |

FOREIGN PATENT DOCUMENTS

| EP | 0775485 A1 * | 5/1997 | A61K 9/14 |
|---|---|---|---|
| JP | 2006-151968 A * | 6/2006 | A61K 31/714 |

OTHER PUBLICATIONS

Machine translation of JP2006-151968A (2006) [online] [Retrieved Apr. 21, 2015] Retrieved from the internet <https://dossier1.j-platpat.inpit.go.jp/tri/all/odse/ODSE_GM101_Top.action>.*
Millichamp, N.J. (1999) Toxicity in Specific Ocular Tissues in "OPHTHALMIC TOXICOLOGY". Edited by George C.Y. Chiou. Published by Taylor & Francis, p. 48-50.*
Shepherd, G., Velez, L.I. (2008) Role of Hydroxocobalamin in Acute Cyanide Poisoning. The Annals of Pharmacotherapy, vol. 42, p. 661-669.*
"Hydrogen Cyanide (HCN)" from the Agency for Toxic Substances & Disease Registry [online] Retrieved from the internet at <https://web.archive.org/web/20100602225537/http://www.atsdr.cdc.gov/MHMI/mmg8.pdf> Published Jun. 2010.*
Ghate, D., Edelhauser, H.F. (2006) Ocular drug delivery. Expert Opinion on Drug Delivery, vol. 3, No. 2, p. 275-287.*
Kuckelkorn, R., Schrage, N., Keller, G., Redbrake, C. (2002) Emergency treatment of chemical and thermal eye burns. Acta Ophthalmologica Scandinavica, vol. 80, p. 4-10.*
Garcia-Valldecabres, M., López-Alemany, A., Refojo, M.F. (2004) pH Stability of Ophthalmic Solutions. Optometry, vol. 75, No. 3, p. 161-168.*
Anes et al.,"Nitritocobalamin and nitrosocobalamin may be confused with sulfitocobalamin using cation-exchange chromatography", Journal of Chromatography B, Biomedical Applications, 1994, 60: 180-185.
Beck Ra at al. , "Picomolar quantitation of free sulfite in foods by means of [57Co]hydroxocobalamin and radiometric chromatography of [57Co]sulfitocobalamin. Method, applications and significance of coexisting sulfides" Journal of Chromatography A, 2000, 881(1-2):345-56.
Begley Ja et al., "Presence of sulfitocobalamin in cell extracts. Resolution and identification by SP-Sephadex C-25 cation exchange chromatography", 1979, pp. 971-974, in Vitamin B12. Eds. B. Zagalak and W. Friedrich. Walter de Gruyter & Co., Berlin. 1212p.
Farquharson J. et al., "Conversion of hydroxo(aquo) cobalamin to sulfitocobalamin in the absence of light: a reaction of importance in the identification of the forms of vitamin B12, with possible clinical significance", American Journal of Clinical Nutrition, 1977, 10:1617-1622.
http://www.morganlens.com/use.html (accessed Jun. 4, 2013, 2010), which describes and exemplifies the use of the Morgan Lens.
Kaczka EA et al., "Vitamin B12. XVI. Modification of cyanocobalamin", Journal American Chemical Society, 1951, 73:3569-3573.
Marcus, A. D., Stanley, Jr (1964) Stability of the Cobalamin Moiety in Buffered Aqueous Solutions of Hydroxocobalamin. Journal of Pharmaceutical Sciences, vol. 53, No. 1, p. 91-92.

(Continued)

Primary Examiner — Layla Berry
(74) Attorney, Agent, or Firm — Lerner, David, Littenberg, Krumholz & Mentlik, LLP

(57) ABSTRACT

Combustion reactions release pollutant gases that associate with ocular fluids and tissues which can have an acute ocular impact. The chronic irritation and chemical effects of these gases also promote ocular aging over the lifespan. Instantaneous pollutant effects can be reduced at the time of eye exposure by using an eyewash (collyrium) composition comprising hydroxocobalamin and/or hydroxo(aquo)cobalamin. Such compositions minimize pollutant gas reactions with ocular tissues by (1) deactivating the gases; and (2) expediting their removal from the eye by, for example, aqueous rinsing and dilution.

9 Claims, No Drawings

(56) References Cited

OTHER PUBLICATIONS

Remington: the Science and Practice of Pharmacy, 19th Edition, editor Alfonso R. Gennaro, published by Mack Publishing Company (1995) p. 1502.
Smith, EL, "Vitamin B12", Methuen & Co., London/John Wiley & Sons, New York, 1960, TOC, pp. 30-31, 38, 39, 54, 55, 130, 131, 164, 165, 192, 193.

* cited by examiner

COLLYRIUM COMPOSITION AND METHOD OF USING SAME

CROSS-REFERENCE TO RELATED APPLICATIONS

This application is a divisional of U.S. application Ser. No. 13/291,687, filed on Nov. 8, 2011, which claims the benefit of the filing date of U.S. Provisional Patent Application No. 61/411,073 filed Nov. 8, 2010, the disclosures of which are hereby incorporated herein by reference.

BACKGROUND OF THE INVENTION

Embodiments of the invention generally relate to environmental medicine, occupational health, industrial hygiene, emergency medicine, ophthalmology, first responder eye protection, and the like. In particular, various aspects of the invention relate to an eyewash or eye drops, both referred to herein as a collyrium, for deactivating irritant and pollutant gases that readily adsorb to exposed ocular tissues, periocular fluids, or contact lenses is particularly useful. When deactivated, these reactive gases have an improved water solubility which enables their removal by aqueous irrigation and rinsing.

The oxidation or combustion of substances can be rapid or slow. Rapid oxidations produce fire, heat, light, and gases. In contrast, rusting iron and biological oxidation examples are slow oxidations; they ordinarily do not display typical evidence of fire, such as heat and light.

Rapid oxidations begin when a combustible material is exposed to an energy source such as heat, electricity, radiation, and the like. When the energy source provides sufficient energy so as to raise the temperature above a unique ignition temperature, the combustible material begins to oxidize or burn without further additional external energy.

One of the simplest and most complete oxidation reactions is exemplified by the reaction of hydrogen and oxygen. These elements readily combust to produce water and heat:

$$2H_2 + O_2 \rightarrow 2H_2O + \text{Heat} \tag{1}$$

Due to the reaction's exothermic nature, the intense release of heat vaporizes newly formed water into steam. This rapid combustion reaction is then complete and the reaction is simple and predictable.

In the absence of controlled laboratory conditions, even the complete oxidation reaction involving hydrogen and oxygen can be difficult to forecast. As combustion reactions proceed under typical ambient conditions, a bewildering array of products can develop. While some obvious combustion products are favored, many minor and trace products can also form. These products may be totally unpredictable or reflect the unique presence of elements within the combustible material. Some of these products may or may not exhibit toxicity.

Whatever the combustion model, the final mixture of reaction products will be influenced by:
(a) Molar amounts of constituent atoms present in the combustible materials;
(b) Thermodynamic conditions driving atomic reactions at the instant of combustion; and/or,
(c) Physical conditions directing equilibria as post-combustion atomic species combine to achieve thermodynamic stability.

Many of these factors are so transient that it may not be possible to predict all combustion products with certainty.

Since combustible organic materials usually include high percentages of carbon atoms, post-combustion equilibrium products favor oxides of carbon. These usually include carbon monoxide (CO) or carbon dioxide ($CO_2$) when combustion occurs under ambient atmospheric conditions.

With vigorous combustion, however, a deficit of oxygen (or oxidizer) favors the formation of partially oxidized carbon which can include soot, ash, or smoke. Furthermore, combustion reactions in air having 78% nitrogen, will promote the added development of nitrogen oxides (NO) and cyanide (CN), while the presence of trace levels of sulfur in the air can result in the formation of sulfur oxides ($SO_x$). Therefore, regardless of the elemental simplicity of reactions involving hydrocarbons based on carbon and hydrogen, the presence of typical atmospheric gases or components can result in the formation of several complicated combustion products.

Survival instincts or autonomic reflexes usually minimize the voluntary inhalation of irritant combustion products which can be responsible for carcinogenic, toxigenic, or irritant respiratory damage. Ocular tissues, including the lens, conjunctiva, and periocular membranes, however, are relatively unprotected from combustion gas product exposures, and they are also liable to chemical attack. While immediate molecular damage to these structures by reactive gases is possible, a cascade of poorly defined secondary reactions often results in delayed tissue damage.

When moist eyes are exposed to reactive gases, eye discomfort is typically described as a burning, dull pain with grittiness, or the feeling of "something in my eye." Few remedies work quickly enough for locating and eliminating the source of such uncomfortable and inaccessible sensations.

While the globe of the eye itself may be a direct pain source, combustion gases are also dispersed over the periocular tissues, which further complicate irritant sensations. Notwithstanding any abrasive effects caused by particulates, eye discomfort is also complicated by pH-induced effects as reactive gases interact with moist ocular membranes.

Because gas combustion products often include acidic anhydrides, these are rapidly converted into acids upon exposure to water such as found in and around the eye. For example, carbon dioxide, nitrogen dioxide, and sulfur dioxide each develop their corresponding acids such as carbonic acid, nitrous (nitric) acid, and sulfurous acid:

$$CO_{2(g)} + H_2O_{(l)} \rightarrow H_2CO_{3(aq)} \tag{2}$$

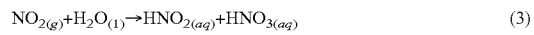

$$NO_{2(g)} + H_2O_{(l)} \rightarrow HNO_{2(aq)} + HNO_{3(aq)} \tag{3}$$

$$SO_{2(g)} + H_2O_{(l)} \rightarrow H_2SO_{3(aq)} \tag{4}$$

Since water is readily available on ocular membranes and in tears, $pK_a$-dictated acid properties effectively lower the pH of aqueous eye fluids. This action promotes an irritant effect over highly innervated ocular tissues along with increased lacrimation.

Typical threats due to fire and combustion products are often met with the urgency of survival. While sensations of smoke, heat, and fire prompt escape and avoidance responses, significant fire events release such large amounts of reactive gases that contact with them is often unavoidable.

Typical among these circumstances are natural gas, industrial, chemical, and wild or forest fires where large volumes of $NO_2$, NO, $SO_2$, and CN are produced. Threats from these gases are particularly serious for first-responders and others at fire scenes largely due to the increased use of synthetic combustible building materials made from or incorporating synthetic compositions including polyacrylonitrile, polyurethane, polyamide, and urea-formaldehyde.

Many of the most injurious gases cannot be avoided since more abundant volatiles mask their presence. In best case scenarios, tissue exposure to reactive gases may be limited by protective equipment, but too often the eyes and their related tissues are inadvertently exposed to biologically active and/or poisonous gases.

Thus, an effective emergency strategy for moderating unavoidable reactive pollutant gas effects on the eyes persists as an unmet need.

Typical treatments often rely on flushing the eyes with an aqueous fluid to displace foreign material. Unfortunately, this has little value for alleviating irritant and reactive gas effects on the eyes since gases interact in at least two ways upon eye contact. First, they adsorb to structural biochemical elements in the eye such as proteins and carbohydrates; and second, they initiate further reaction cascades that support cumulative sight-compromising outcomes if unchecked. Presently available collyria (i.e., eyewashes) fail to address either one of these issues.

BRIEF SUMMARY OF THE INVENTION

A collyrium composition comprising hydroxocobalamin, hydroxo(aquo)cobalamin or a mixture of hydroxocobalamin and hydroxo(aquo)cobalamin, the mixture sometimes referred to herein in a shorthand manner as hydroxocobalamin, which is particularly useful for substantially deactivating reactive pollutant combustion gases adsorbed to eye surfaces, periocular tissues and gas permeable contact lenses. When deactivated, the reaction product of such reactive gases with hydroxocobalamin has improved water solubility which enables their removal by aqueous irrigation and rinsing.

DETAILED DESCRIPTION

In addition to their physical adsorption and biochemical reactivity with ocular proteins, mucins, and carbohydrates, several gases also serve as gasotransmitters which cause eye inflammation, irritation, and general discomfort.

Some reactive combustion products including hydrogen cyanide (HCN) in particular, are commonly recognized as acute poisons. For HCN, its lethal effects occur at the level of cytochrome oxidase in oxidative phosphorylation, but it supports many other destructive reactions including structural disruptions of thiols responsible for maintaining the conformational framework of bioactive proteins.

In addition to being widely associated with smoker's amblyopia and optic neuropathy, cataractogenesis studies further link cyanide with dysfunctional $Ca^{2+}$-ATPase activity. This enzyme usually ensures calcium homeostasis within the lens, cornea, and vitreous humor. Cyanide also exhibits disruptive effects on nerve function and plays a role in promoting demyelination. There are also biochemical interactions of cyanide, cobalamins and vitamin $B_{12}$ in particular.

Other toxic combustion products include sulfur dioxide ($SO_2$) which is associated with eye irritation and conjunctivitis. While serious structural damage to the eye depends on $SO_2$ exposure frequencies, gas concentration, and lengths of exposure time, cumulative ocular membrane damage effects involve its reactivity with nucleophilic π-electron-containing structures. These occur as unsaturated sites on alkyl and aromatic structures or unsaturated bond sites critical to membrane architecture. While irritant and degenerative eyesight effects are linked to $SO_2$ exposure, advanced degenerative scenarios reflect cumulative effects on all ocular tissues as opposed to a single targeted effect shown by cyanide.

Separate from $SO_2$ reactivity, hydrogen sulfide and hydrosulfide (respectively, $H_2S$ and $HS^-$) similarly impair electron flow like $CN^-$ at the level of oxidative phosphorylation since $H_2S$ is a significant reducing agent. The outcome of this respiratory asphyxiation may be realized as localized tissue necrosis or systemic death on a par with $CN^-$.

With respect to actions on ocular tissues, it is likely that sulfides react with alkali elements on moist tissues to produce caustic sodium sulfide (NaS). Thus, the mélange of physiological and biochemical disruptions results in ocular hypersensitivity to light, blurred vision, or other visual disturbances.

Nitric oxide (NO) on the other hand, modulates vascular dilation and constriction dynamics as well as irritant inflammatory mechanisms in animals. Although NO was first identified as the endothelial relaxation factor (EDRF), its powerful actions as a gasotransmitter are now well established along with hydrogen sulfide ($H_2S$) and carbon monoxide (CO).

Gasotransmitters are small endogenously produced gas molecules that exert powerful physiological effects on tissues. Because of their critical roles and extreme potency at low molar concentrations, their physiological presence is tightly regulated by enzymatic and signaling queues.

As with many poisonous substances, the gasotransmitters like NO are critical for signaling essential aspects of animal biochemistry and physiology, but uncontrolled levels occurring as environmental pollutants can be destructive or lethal.

While essential for normal physiology, NO studies confirm its role in septic shock, hypertension, cerebral ischemia, chronic degenerative nervous system disorders, maintaining vascular tone, neurotransmission, immune responses, and cytotoxicity.

NO also exerts homeostatic processes in the eye while regulating aqueous humor dynamics, retinal neurotransmission, and phototransduction. Furthermore, uncontrolled changes in NO availability can incite inflammatory disorders including uveitis, retinitis, or degenerative disease roles linked to glaucoma and retinal degeneration.

Although NO can be a potentially lethal or toxic compound, its toxicity is likely related to its oxidative transformation into peroxynitrite ($ONOO^-$). Thus, NO is an initiator that paves the way for later disruptive reactions involving both nucleophilic and electrophilic species. The wide array of potentially destructive tissue chemistry supported by uncontrolled NO sources from fires and occupational hazard areas justifies its mandatory control in the workplace.

Exclusive of peroxynitrite formation, NO can be converted into nitrogen dioxide ($NO_2$) and then nitrous acid ($HNO_2$) if eye moisture is available. Each of these products reacts in various ways to damage ocular systems which, when damaged, are slow to repair, if at all possible.

The disruptive biochemistry of the above-described gas combustion products is well known, but their long-term low-level chronic exposure affects as sight-compromising factors over a typical lifespan have not been appreciated or accurately characterized. More importantly, there does not exist an effective strategy or effective composition for decreasing their reactivity with ocular tissues.

Reactive gases are deactivated or substantially deactivated upon their exposure to hydroxocobalamin which converts them into cobalamin-adducts. Reactive pollutant gases of interest include sulfur dioxide ($SO_2$), sulfur trioxide ($SO_2$), nitric oxide (NO), nitrogen dioxide ($NO_2$), nitrous oxide ($N_2O$), hydrogen sulfide ($H_2S$), thiols (—SH), polysulfides (S—$[S]_n$—S), monosulfides ($S^-$), and cyanide (CN). These gases are common atmospheric pollutants in workplaces, the environment, and fire scenes.

Conventional versions of collyria employ aqueous buffered saline solutions with or without additives for washing or flushing the eyes. They help relieve eye dryness and minor irritation, typically in connection with flushing foreign particulate material (i.e., dust or pollen) from the eyes. Solutes including salts and organic materials removed from the eye are limited by their solubility in the liquid phase of the collyrium. Current collyria may also contain metal ion chelators such as disodium ethylene diamine tetraacetic acid (disodium EDTA) and preservatives.

None of the existing commercial collyria can deactivate irritants or reactive gases released by combustion. Not only are these irritant gases typically reactive, but several are biochemically toxic at low levels. Added to this, many adsorb to structural elements of the eye and periocular tissues to initiate damaging localized tissue effects.

Thus, simple flushing of the eye with a buffered aqueous fluid or one with a simple chelate affords little benefit for intercepting toxic reactive gases or reinstating normal conditions to the eye or its periocular tissues.

The present disclosure relates to collyria compositions comprising hydroxocobalamin (HO-Cbl) and its pharmaceutically and physiologically acceptable derivatives (the term "acceptable" meaning where, for example, such compounds are introduced to the eye) or mixtures thereof as active pharmaceutical ingredients (APIs). Hydroxocobalamin, also known as vitamin $B_{12a}$, originates from vitamin $B_{12}$ or cyanocobalamin (CN-Cbl) upon the loss of its cyanide moiety by photolysis or suitable reducing conditions. The vitamin $B_{12a}$ is then presumed to carry a hydroxyl group in place of the lost cyanide which warrants its common designation as hydroxocobalamin (HO-Cbl) (Smith, 1960). The hydroxyl group of hydroxocobalamin (also sometimes referred to as vitamin $B_{12a}$), may then become tautomeric upon the attachment of a water molecule to the sixth coordinate bond of the cobaltic ion to give aquocobalamin, which is also sometimes referred to as vitamin $B_{12b}$. Aquocobalamin is also sometimes referred to as hydroxo(aquo)cobalamin or designated as aquacobalamin (Id.). Both hydroxocobalamin and hydroxo(aquo)cobalamin are suitable for use herein and are also referred to herein generically as hydroxocobalamin. The systematic IUPAC name or designation of hydroxocobalamin is Coα-[α-(5,6-dimethylbenzimidazolyl)]-Coβ-hydroxocobamide, its chemical composition is $C_{62}H_{90}CoN_{13}O_{15}P$, and its structure has been represented as follows:

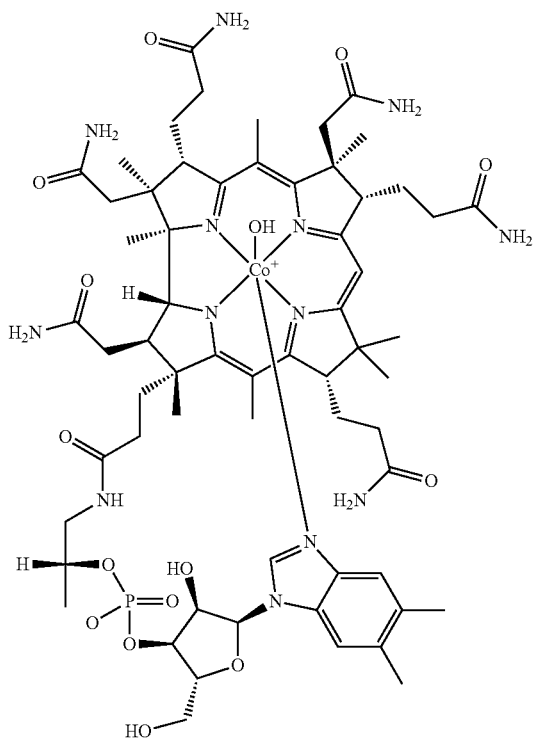

Upon administration of a collyrium composition of the present invention, for example comprising hydroxocobalamin in a fluid carrier such as water, the hydroxocobalamin is able to form new adducts with reactive pollutant gases, such as those described above. Once formed, such cobalamin-adducts of pollutant gases show reduced tissue-binding tendencies, and preferred occurrences as water-soluble cobalamin-adducts. This has an immediate benefit for (a) limiting localized irritant actions, (b) curtailing irritant concentrations on tissue surfaces, (c) reducing biochemical insults to tissues, and (d) enhancing the dilution and flushing of gaseous species from ocular tissues.

Collyria compositions of the present invention are preferably fluid compositions, more preferably substantially aqueous compositions comprising hydroxocobalamin and pharmaceutically acceptable derivatives of hydroxocobalamin. Alternatively, the fluid composition may comprise a fluid carrier in addition to water, provided such fluid is chemically, physiologically and otherwise compatible with the eye and its components and structures.

Such a protective mechanism reflects the transition metal chemistry of cobalt exhibited by four coordination bonds within the corrin ring of hydroxocobalamin (HO-Cbl). Under this condition, cobalt readily forms adducts to negatively charged species at acidic conditions of about 5.2 pH (Anes et al., 1994, Beck et al., 2000).

Cyanide shows the strongest formation constant of all adduct forms by producing the cyanocobalmin adduct (CN-Cbl) also known as vitamin $B_{12}$.

Hydroxocobalamin occurs naturally in animal tissues at low concentrations, but for commercial applications, its bulk manufacture partly depends on synthetic steps.

This reaction was first described in the early 1950s (Kaczka et al, 1951, Smith, 1960), and solutions of hydroxocobalamin were later proposed to combat cyanide poisoning and to diagnose chronic hypercyanogenesis (U.S. Pat. No. 3,903,253).

Once formed in the body, the cyanide held in CN-Cbl is rapidly excreted in the urine, which can avoid acute poisoning.

Beyond the reaction of cyanide with hydroxocobalamin, other substances also produce adducts to HO-Cbl but they are not well known (Smith, (1960)). They include several of the pollutant gases described hereinabove and associated with ocular irritation, sensitivity, and tissue reactions. Distinct from these actions which can impair sight, several gases also have gasotransmitter effects on highly innervated ocular tissues and vasculature, also as discussed. The existence of these other HO-Cbl adducts has been reported by Begley et al. (1979), Anes et al. (1994) and Beck et al. (2000).

Included among the various reactive combustion gases besides cyanide are $SO_2$, NO, $NO_2$, nitrous oxide ($N_2O$), $H_2S$, thiols (—SH) and various mercaptans. Over the pH range from 4.5-6.0 any of these gases dissolved in tears can interact with HO-Cbl to give corresponding adducts.

For example, $SO_2$ reacts with HO-Cbl to produce sulfitocobalamin, $SO_2$-cobalamin (reported by Farquharson (1977)). The formation constant for this adduct is second only to that for CN-Cbl formation.

$NO_2$ reacts with HO-Cbl to produce nitritocobalamin ($NO_2$-cobalamin), while NO reacts with HO-Cbl to produce nitrosyl- or nitrosocobalamin (NO-cobalamin). NO-cobalamin further appears to be readily converted to $NO_2$-cobalamin thereby averting the formation of peroxynitrite ($ONOO^-$) in some cases.

Thiols and mercaptans react with HO-Cbl to give detectable cobalamin sulfides.

In each of these instances, the biologically significant or chemically reactive gas results in a water-soluble adduct to HO-Cbl with reduced activity for adsorbing to or reacting with ocular tissues. This enables the pollutant gases to be flushed from the eyes and related tissues by rinsing or irrigation.

Viscosity of collyrium compositions comprising hydroxocobalamin and disclosed herein can be formulated to exhibit viscosities suitable for use as protective ophthalmic drops. When distributed over the eye, the hydroxocobalamin of such eye drops preferentially intercepts reactive and toxic pollutant gases before they can adsorb to eye tissues and/or be dissolved or dispersed in eye fluids. Thus the present invention provides a counter-measure or buffer against irritant factors that may exacerbate, for example, syndromes or conditions referred to as "dry eye". In the absence of the present invention, reactive irritant gases, especially sulfur oxides, have an unhindered ability to adsorb to and react with moisture deficient ocular tissues which initiates significant tissue damage. Viscosities of the compositions of the present invention can be varied using generally accepted ocular excipients so that the viscosity of such collyria are, for example, equal to or greater than water. Examples of suitable excipients include natural hydrogels, synthetic polymers and the like which exhibit varying degrees of aqueous solubility or solubility in the hydroxocobalamin-containing compositions. Thus, by varying the viscosity of the present compositions, the contact time of the collyrium with ocular tissues can be varied as well as its ability to bathe periocular tissues in the posterior regions of the eye which can be difficult to access.

The present invention also provides a method for deactivating reactive pollutant combustion gases present in ocular fluid or adsorbed to eye surfaces, periocular tissues, and gas permeable contact lenses such as by applying or introducing a collyrium composition comprising hydroxocobalamin to the eye. The method is suitable for use in combination with a Morgan Lens (available, for example, from MorTan, Inc., Missoula, Mont. 59807-8719) which provides a convenient apparatus to bathe the eye with the collyrium composition of the invention (see for example, http://www.morganlens.com/use.html (accessed Nov. 3, 2010), which describes and exemplifies the use of the Morgan Lens). With or without the use of a Morgan Lens upon deactivating irritant gases the eye can be irrigated with additional collyrium composition, aqueous fluids or both collyrium composition and aqueous fluids to flush pollutant species from the eye in the form of cobalamin adducts.

Collyrium compositions of the present invention comprise hydroxocobalamin suitable for application to the eye. In particular, since combustion gases from smoking or environmental sources can negatively affect normal tissue cobalamin distributions, compositions of the present invention can provide a directed, further supply of cobalamin via the introduction of hydroxocobalamin to ocular tissues without the need for injections.

While emergency clinical treatments involving acute cyanide poisoning can be combated with 1-5 gram intravenous doses of HO-Cbl (Pouchol et al., U.S. Pat. No. 5,834,448), no ophthalmic application has been disclosed for detoxifying adsorbed or reactive gas combustion products on ocular tissues or in ocular fluids. Distinct from HO-Cbl reactions that render CN ineffective as a poison, HO-Cbl has never been used as an API for therapeutically scavenging CN from the eyes in the capacity of a collyrium. Beyond this, the use of HO-Cbl to mitigate the immediate consequences of reactive nitrogen and sulfur pollutant gases with ocular tissues has never been described.

Specific formulations or compositions comprising hydroxocobalamin and/or aquocobalamin are also envisioned. The formulations are intended to be functional while being sensitive to cost at both the ingredient and manufacturing levels. Typical compositions comprise hydroxocobalamin or aquocobalamin in an amount of about 0.001 wt. % to about 2.0 wt. %; preferably about 0.01 wt. % to about 1.5 wt. %; more preferably about 0.02 wt. % to about 1.0 wt. %, most preferably about 0.03 wt. % to about 0.5 wt. %; such as about 0.04 wt. % to about 0.25 wt. %; for example, about 0.05 wt. %. Eye drop formulations and suitable excipients useful in such formulations are well-known in the art. A general reference describing typical excipients useful in ocular dosage forms can be found in "Pharmaceutics-Dosage Form and Design", D. Jones, Pharmaceutical Press, London, 2008, Chapter 6, pages 135-156. Eye drops or other ophthalmic preparations are known to one of skill in the art. See, e.g., *Remington's Pharmaceutical Sciences*, $20^{th}$ ed., Mack Publishing, Easton Pa. (2,000); and *Introduction to Pharmaceutical Dosage Forms*, 4th ed., Lea & Febiger, Philadelphia (1985). The contents of these references are incorporated herein by reference to the extent permitted.

Preferred or typical excipient ingredients can include those that impart: (1) aqueous viscosity control such as dextrans, hyaluronic acid, modified celluloses and the like; (2) buffering action compatible with the presence of hydroxocobalamin over the eye; (3) moisturizing and/or lubricating actions; and (4) ocular redness relievers such as tetrahydrozoline, and/or (5) mild anti-inflammation agents. A wide range of excipients and excipient concentrations known to those skilled in the art can be used provided that selected excipients do not react with hydroxocobalamin or aquocobalamin to interfere with its chemical actions to form adducts with or bind with or otherwise render ineffective reactive pollutant gases.

This disclosure and its principles provide a basis for various alternative embodiments, including, for example:

1. A collyrium composition comprising hydroxocobalamin.
2. The composition of paragraph 1 further comprising pharmaceutical excipients suitable for application to or contact with the eye and its component fluids and structures.
3. The composition of paragraph 1 suitable for deactivating reactive pollutant combustion gases adsorbed to eye surfaces, periocular tissues, and gas permeable contact lenses.
4. A method for deactivating reactive pollutant combustion gases present in ocular fluid or adsorbed to eye surfaces, periocular tissues, and gas permeable contact lenses comprising applying a collyrium composition comprising hydroxocobalamin to the eye.
5. The method of paragraph 4 further comprising the use of a Morgan lens.
6. The method of paragraph 4 or 5 wherein upon deactivating irritant gases, the eye is irrigated with additional collyrium composition, aqueous fluids or both collyrium composition and aqueous fluids to flush pollutant species from the eyes in the form of cobalamin adducts.
7. The collyrium composition of paragraph 1 suitable for deactivating irritant gases adsorbed to gas permeable contact lenses for decontamination purposes.
8. A collyrium composition comprising hydroxocobalamin formulated to exhibit viscosity suitable for use as protective ophthalmic drops.
9. A collyrium composition comprising hydroxocobalamin suitable for application to the eye.

In each of the alternative embodiments described herein it is to be understood that a reference to hydroxocobalamin also includes its equivalent pharmaceutical and physiologically acceptable derivative identified as hydroxo(aquo)cobalamin, which may be introduced into the eye.

DEFINITIONS

As used herein the following terms or phrases have the indicated meanings.

The term "about" when used as a modifier for, or in conjunction with, a variable, characteristic or condition is intended to convey that the numbers, ranges, characteristics and conditions disclosed herein are flexible and that practice of the present invention by those skilled in the art using concentrations, amounts, contents, properties such as solubility, etc., that are outside of the stated range or different from a single stated value, will achieve the desired result or results as described in the application, namely, collyria compositions comprising hydroxocobalamin and/or aquocobalamin and their uses as described herein.

"Comprise" or "comprising": Throughout the entire specification, including the claims, the word "comprise" and variations of the word, such as "comprising" and "comprises," as well as "have," "having," "includes," "include" and "including," and variations thereof, means that the named steps, elements, components or materials to which it refers are essential, but other steps, elements, components or materials may be added and still form a construct within the scope of the claim or disclosure. When recited in describing the invention and in a claim, it means that the invention and what is claimed is considered to be what follows and potentially more. These terms, particularly when applied to claims, are inclusive or open-ended and do not exclude additional, unrecited elements, components or methods steps.

"Substantially": Unless otherwise defined with respect to a specific property, characteristic or variable, the term "substantially" as applied to any criteria, such as a property, characteristic or variable, means to meet the stated criteria in such measure such that one skilled in the art would understand that the benefit to be achieved, or the condition or property value desired is met.

All documents described herein are incorporated by reference herein, including any patent applications and/or testing procedures. The principles, preferred embodiments, and modes of operation of the present invention have been described in the foregoing specification.

Further, any range of numbers recited in the specification or claims, such as that representing a particular set of properties, units of measure, conditions, physical states or percentages, is intended to literally incorporate expressly herein by reference or otherwise, any number falling within such range, including any subset of numbers within any range so recited. For example, whenever a numerical range with a lower limit, $R_L$, and an upper limit $R_U$, is disclosed, any number R falling within the range is specifically disclosed. In particular, the following numbers R within the range are specifically disclosed:

$$R=R_L+k(R_U-R_L),$$

wherein k is a variable ranging from 1% to 100% with a 1% increment, e.g., k is 1%, 2%, 3%, 4%, 5% . . . 50%, 51%, 52% . . . 95%, 96%, 97%, 98%, 99%, or 100%. Moreover, any numerical range represented by any two values of R, as calculated above is also specifically disclosed.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

REFERENCES

Anes J M, Beck R A, Brink J J, Goldberg R J. 1994. Nitritocobalamin and nitrosocobalamin may be confused with sulfitocobalamin using cation-exchange chromatography. Journal of Chromatography B, Biomedical Applications. 660: 180-185.

Beck R A, Anes J M, Savini L M, Mateer R A. 2000. Picomolar quantitation of free sulfite in foods by means of [$^{57}$Co]hydroxocobalamin and radiometric chromatography of [$^{57}$Co]sulfitocobalamin. Method, applications and significance of coexisting sulfides Journal of Chromatography A. 881(1-2):345-56.

Begley J A, Hall C A. 1979. Presence of sulfitocobalamin in cell extracts. Resolution and identification by SP-Sephadex C-25 cation exchange chromatography. Pp 971-974. In Vitamin B$_{12}$. Eds. B. Zagalak and W. Friedrich. Walter de Gruyter & Co., Berlin. 1212 p.

Farquharson J, Adams J F. 1977. Conversion of hydroxo (aquo) cobalamin to sulfitocobalamin in the absence of light: a reaction of importance in the identification of the forms of vitamin $B_{12}$, with possible clinical significance. American Journal of Clinical Nutrition. 10:1617-1622.

Kaczka E A, Wolf D E, Kuehl F A, Folkers K. 1951. Vitamin $B_{12}$. XVI. Modification of cyano-cobalamin. Journal American Chemical Society. 73:3569-3573.

Smith, E L. 1960. Vitamin $B_{12}$. Methuen & Co., London/John Wiley & Sons, New York. 196 p.

U.S. Pat. No. 3,903,253, M. Rolland, "Process for Diagnosing Hypercyanogenesis"

U.S. Pat. No. 5,834,448, Pouchol, et al., "Dosage Form of Hydroxocobalamin and its Use in Cyanide Poisoning"

http://www.morganlens.com/use.html (accessed Nov. 3, 2010), which describes and exemplifies the use of the Morgan Lens

The invention claimed is:

1. A method comprising:
   applying a protective or decontaminating collyrium composition to a fluid, structure or tissue selected from the group consisting of ocular fluid, eye surfaces, periocular tissues, and contact lenses;
   said composition comprising a compound selected from the group consisting of hydroxocobalamin, hydroxo(aquo)cobalamin or a mixture of hydroxocobalamin and hydroxo(aquo)cobalamin;
   wherein said protective or decontaminating collyrium composition deactivates or substantially deactivates or facilitates removal of irritant gases or reactive pollutant combustion gases for individuals in need thereof.

2. The method of claim 1 further comprising the use of a Morgan lens.

3. The method of claim 1 wherein upon deactivating irritant gases, the eye is irrigated with additional collyrium composition, aqueous fluids or both collyrium composition and aqueous fluids to flush pollutant species from the eyes in the form of cobalamin adducts.

4. The method of claim 1, the collyrium composition further comprising pharmaceutical excipients suitable for application to or contact with the eye and its component fluids and structures.

5. The method of claim 4, the composition formulated to exhibit viscosity suitable for use as ophthalmic drops.

6. The method of claim 1, the composition comprising about 0.001 wt. % to about 2.0 wt. % hydroxocobalamin, hydroxo(aquo)cobalamin or both hydroxocobalamin and hydroxo(aquo)cobalamin.

7. The method of claim 1 wherein the collyrium composition exhibits a pH from 4.5-6.0.

8. The method of claim 1 wherein the contact lens is a gas permeable contact lens.

9. The method of claim 1 wherein irritant gases or reactive pollutant combustion gases are selected from the group consisting of sulfur dioxide, sulfur trioxide, nitric oxide, nitrogen dioxide, nitrous oxide, hydrogen sulfide, compounds containing a thiol group, compounds containing a monosulfide group, compounds containing a hydrosulfide group, compounds containing a cyanide group and compounds containing polysulfides.

* * * * *